United States Patent [19]

Wehner et al.

[11] Patent Number: 4,764,468
[45] Date of Patent: Aug. 16, 1988

[54] PROCESS FOR STABILIZING THE ACTIVITY OF PEROXIDASE IN SOLUTION

[75] Inventors: Rainer Wehner, Gauting; Johann Mattersberger, Munich; Dagmar Klenner, Tutzing; Gerlinde Deutsch-Weyer, Bernried, all of Fed. Rep. of Germany

[73] Assignee: Boehringer Mannheim GmbH, Mannheim, Fed. Rep. of Germany

[21] Appl. No.: 835,895

[22] Filed: Mar. 4, 1986

[30] Foreign Application Priority Data

Mar. 14, 1985 [DE] Fed. Rep. of Germany ....... 3509238

[51] Int. Cl.$^4$ .......................... C12N 9/96; C12N 9/08; C12Q 1/28
[52] U.S. Cl. ..................................... 435/188; 435/28; 435/192
[58] Field of Search .......................... 435/192, 28, 188

[56] References Cited

U.S. PATENT DOCUMENTS

| | | | |
|---|---|---|---|
| 4,378,429 | 3/1983 | Modrovch | 435/28 X |
| 4,503,144 | 3/1985 | Deeg et al. | 435/28 X |
| 4,504,579 | 3/1985 | Sun | 435/28 |
| 4,517,287 | 5/1985 | Scheibe et al. | 435/28 X |

OTHER PUBLICATIONS

Fujiwara et al. in Chemical Abstracts vol. 104 1986 Abstract No. 147015h of Japan Kokai 60,192,260 published Sep. 30, 1985.

*Primary Examiner*—Lionel M. Shapiro
*Attorney, Agent, or Firm*—Felfe & Lynch

[57] ABSTRACT

The present invention provides a process for stabilizing the activity of peroxidase in solution by the addition of a specific activity stabilizer, wherein, to the enzyme present in solid or dissolved form, there is added, as activity stabilizer, phenol which optionally contains one or more substituents selected from lower alkyl radicals and chlorine and bromine atoms, in an amount of from 0.0005 to 2% by weight, referred to the solution.

13 Claims, No Drawings

PROCESS FOR STABILIZING THE ACTIVITY OF PEROXIDASE IN SOLUTION

The present invention is concerned with a process for stabilising the activity of peroxidase in solution.

Peroxidase is a widely used enzyme, especially for enzymatic detection reactions. Peroxidase has also found wide use as a labelling enzyme for the numerous forms of enzyme immune tests (EIA). Peroxidases of various origins and especially horseradish peroxidase can be detected quickly and quantitatively by a number of methods.

Upon this is based the very good suitablility of peroxidases as a detection and labelling enzyme. On the other hand, however, peroxidase suffers from the disadvantage that it does not have a completely satisfactory stability, especially in comparatively high dilution and in solution. Therefore, the period of life of especially peroxidase conjugates in enzymatic test reagents or in other enzyme preparations is limited and a stabilisation is necessary in order to achieve the desired storage stability.

It is already known from Federal Republic of Germany Patent Specification No. 31 00 076 to stabilise peroxidase in a medium containing serum protein by the addition of 8-anilino-1-naphthalenesulphonic acid (ANS). From European Patent Specification No. 0,070,992, it is known to use 4-aminoantipyrine for the stabilization of peroxidase in a serum or in a medium containing serum protein. Finally, from U.S. Pat. No. 4,169,012, it is known to stabilize peroxidase by means of polyvalent ions of Groups III and IV of the Periodic System, for example aluminium, zinc, magnesium, iron and copper. However, these known activity stabilizers have a poor compatibility with other components of conventional reagent combinations or still leave something to be desired with regard to the activity stabilization. Furthermore, they sometimes have a negative influence on immune reactions when the peroxidase is present as a conjugate with an immunologically-active substance, which results in very flat calibration curves.

Therefore, it is an object of the present invention to stabilize the activity of peroxidase or of peroxidase conjugates in solution without the above-mentioned disadvantages and without a disadvantageous influencing of the actual immune reaction.

Thus, according to the present invention, there is provided a process for stabilizing the activity of peroxidase in solution by the addition of a specific activity stabilizer, wherein, to the enzyme present in solid or dissolved form, there is added, as activity stabilizer, phenol which optionally contains one or more substituents selected from lower alkyl radicals and chlorine and bromine atoms, in an amount of from 0.0005 to 2% by weight, referred to the solution.

According to the present invention, the enzyme activity of free peroxidase or of peroxidase possibly also present covalently bound in a conjugate is stabilized against the inactivating influence of temperature, foreign substances and the like, which is especially very marked in dilute solutions. This means that the rapid decrease of the enzyme activity occuring in solution is overcome or is very considerably reduced without the immunological effectiveness of an immunologically-active substance bound to the peroxidase in a conjugate being impaired.

As activity stabilizer according to the present invention, there is used phenol per se or a derivative thereof which is substituted with one or more substituents selected from lower alkyl radicals and chlorine or bromine atoms. Apart from phenol per se, preferred stabilizers include bromophenol, chlorophenol, dichlorophenol, dibromophenol and cresol, the substituents hereby being present in all possible positions of the aromatic ring. Of the substituted phenols, those are preferred with one or two substituents in the aromatic ring. Lower alkyl radicals in the scope of the present invention there are to be understood to contain up to 3 carbon atoms.

As already mentioned, the activity stabilizer used according to the present invention is added in an amount of from 0.0005 to 2% by weight, referred to the volume of the solution. In the case of exceeding the upper limit of 2%, the stressability towards the action of heat is, as before, maintained but the peroxidase activity itself is again reduced. Below the lower limit, a satisfactory stabilization is no longer achieved. The activity stabilizer used according to the present invention is preferably added in an amount of from 0.01 to 0.5% by weight.

The activity stabilizer can be added at any desired point of time to the enzyme or enzyme conjugate present in solid or dissolved form. It is preferable to make the addition to a solution since a more uniform distribution of the stabilizer and thus a better action even in the case of additions close to the lower limit of the effective range is hereby achieved. In particular, the phenol can be added to the enzyme or conjugate solution before lyophilization or after reconstitution of the lyophilizate with an aqueous solvent. In the latter case, the solvent can, of course, first also be mixed with the activity stabilizer and then added to the lyophilizate for dissolving it.

As immunologically-effective substance in the conjugate, there is preferably used an antibody or a fragment thereof, an antigen or a hapten.

As antigens or haptens, there can be used, for example, proteins, drugs, steroids and hormones, examples thereof including TBG, cortisol, vitamin B12, digoxin, digoxigenin, triiodothyronine and thyroxin.

As antibodies, there can be used polyclonal and monoclonal antibodies and the fragments thereof. Chemically changed derivatives thereof, for example antibodies cross-linked with glutardialdehyde, can also be components of the conjugate. Examples thereof include antibodies against TSH, hCG, AFP, LH, FSH, prolactin, ferritin, CEA and insulin.

As peroxidase, there can be used all types of this enzyme. Because of its ready availability, horseradish peroxidase is preferred.

In the case of the process according to the present invention, besides the mentioned activity stabiliser, it is preferable also to add a preserving agent. Appropriate preserving agents include, for example, merthiolate, Germall, Dowicil and Kathon CG.

The present invention also provides a stabilized enzyme preparation with a content of peroxidase or of a peroxidase conjugate, wherein it contains 0.0005 to 2% by weight of phenol which optionally contains one or more substituents selected from lower alkyl radicals and chlorine and bromine atoms.

With regard to the components of the conjugate, the amount of the activity stabilizer and a possible content of additional preserving agents, the statements made hereinbefore regarding the process apply equally to the stabilized enzyme preparation. Furthermore, the enzyme preparation preferably also contains a buffer substance, for example phosphate, citrate or borate buffer or the like, and/or bovine serum albumin and/or a system for the detection of peroxidase activity.

The present invention makes possible a stabilization of the enzyme activity of peroxidase and of peroxidase conjugates against the rapid decrease of activity which normally takes place in solution, without adversely influencing the immune reaction in the case of conjugates. According to the present invention, the activity stabilization also takes place at elevated temperatures over a comparatively long period of time so that the usefulness of solutions ready for use of peroxidase and of peroxidase conjugates is considerably improved.

The following Examples are given for the prupose of illustrating the present invention:

EXAMPLE 1

Stabilization of antibody-peroxidase conjugate

Solution 1—incubation buffer

| phosphate buffer (pH 6.9) | 15 mmol/l. |
|---|---|
| bovine serum albumin (BSA) | 0.2% by wt. |
| merthiolate | 0.01% by weight |

Solution 2

| anti-TSH—POD conjugate dissolved in solution 1 | about 40 U/l. |
|---|---|

Solution 3—substrate/buffer solution

| phosphate-citrate buffer (pH 4.4) | 95 mmol/l. |
|---|---|
| sodium perborate | 3.1 mmol/l. |
| 2,2'-azino-di-(3-ethylbenz-thiazoline-6-sulphonic acid) (ABTS) | 1.6 mmol/l. |

The solutions used, coated test tubes and standards originate from the Enzymune test TSH of Boehringer Mannheim GmbH (Order No. 73 60 83). The determination is carried out analogously to the manufacturer's instructions.

0.2 ml. TSH standard (about 50 μU/ml.) is introduxed into test tubes coated with anti-TSH antibodies and incubated for 60 minutes at 20° to 25° C. After sucking out and rinsing, 1 ml. of Solution 2 are introduced. The Solution 2 used for this purpose is either freshly prepared (comparative measurement) or has been incubated at 30° C. for 8, 18 or 25 hours prior to use, whereby 0.01% by weight phenol has optionally been added thereto. After incubation for 60 minutes at 20° to 25° C., the test tubes are sucked out and rinsed. Subsequently, 1 ml. of Solution 3 is added thereto and further incubated for 60 minutes at 20° to 25° C. Thereafter, a photometric determination is carried out at λ=405 nm against Solution 3 as blank.

The values set out in the following Table I are, in each case, referred to the relative value of 100% which is obtained with a test in which freshly prepared Solution 2 (without phenol) is used.

Analogous measurements are carried out with

| Enzymun-Test Ferritin | Order No. 67 73 37 |
|---|---|
| Enzymun-Test TBK | Order No. 24 94 16 |
| Enzymun-Test Digoxin | Order No. 19 96 56 |
| Enzymun-Test AFP | Order No. 71 14 11 |

(Producer: Boehringer Mannheim GmbH).

TABLE I

| | 0 hr. | | 8 hrs. | | 18 hrs. | | 24 hrs. | |
|---|---|---|---|---|---|---|---|---|
| phenol 0.01% by wt. | + | − | + | − | + | − | + | − |
| Anti-TSH-POD | 100 | — | — | — | 90 | 21 | — | — |
| Anti-Ferritin-POD | 100 | — | 97 | 62 | — | — | 90 | 40 |
| T₄—POD (TBK-Test) | 100 | — | — | — | — | — | 70 | 4 |
| Digoxin-POD | 100 | — | 99 | 77 | — | — | 93 | 48 |
| Anti-AFP—POD | 100 | — | 96 | 89 | — | — | 86 | 70 |

EXAMPLE 2

Stabilization of free peroxidase with phenol/phenol derivatives.

Incubation buffer:

| potassium dihydrogen phosphate buffer (pH 7.5) | 10 mmol/l. |
|---|---|
| sodium chloride | 100 mmol/l. |
| BSA | 0.5% by wt. |
| phenol or phenol derivative | 0.02% by wt. |

Peroxidase is stressed in incubation buffer for 24 and 48 hours at 30° C. and subsequently the peroxidase activity is determined and compared with the activity of unstressed solutions (unstressed solutions are ones which have been kept at 4° C. for 24 and 48 hours).

For the determination of the peroxidase activity, 0.1 ml. of incubation buffer and 2.9 ml. of peroxidase solution are mixed at 25° C., the change of extinction is monitored photometrically at λ=405 nm for 5 minutes and ΔE/min. determined. The peroxidase activity is calculated as follows:

$$POD \text{ activity} = \frac{100 \times 3}{0.1 \times 36.1 \times 1} \times \Delta E/\text{min. [mU/ml.]}$$

The results obtained are set out in the following Tables II and III:

TABLE II

| | POD-activity (mU/ml) | |
|---|---|---|
| stabilizer | unstressed | 48 hrs./30° C. |
| without stabiliser | 117 | 43 |
| 0.02% phenol | 130 | 130 |
| 0.02% 4-bromophenol | 143 | 140 |
| 0.02% 4-chlorophenol | 140 | 135 |
| 0.02% 2,3-dichlorophenol | 130 | 120 |
| 0.02% 2,4-dichlorophenol | 150 | 135 |
| 0.02% 2,5-dichlorophenol | 130 | 125 |
| 0.02% 3,4-dichlorophenol | 140 | 135 |
| 0.02% 3,5-dichlorophenol | 140 | 125 |

TABLE III

| | POD-activity (mU/ml) | |
|---|---|---|
| stabilizer | unstressed | 24 hrs./30° C. |
| without stabiliser | 22.0 | 16.7 |
| 0.01% o-cresol | 21.6 | 21.2 |
| 0.1% o-cresol | 17.5 | 17.5 |
| 0.01% m-cresol | 22.0 | 22.4 |
| 0.1% m-cresol | 20.4 | 20.8 |
| 0.01% p-cresol | 24.9 | 24.1 |

TABLE III-continued

| stabilizer | POD-activity (mU/ml) | |
|---|---|---|
| | unstressed | 24 hrs./30° C. |
| 0.1% p-cresol | 24.1 | 24.1 |

EXAMPLE 3

Using the test procedure according to Example 2 with phenols of differing concentration, there are obtained the results set out in the following Table IV:

TABLE IV

| stabiliser | POD-activity (mU/ml) | |
|---|---|---|
| | unstressed | 24 hrs./30° C. |
| 0.001% phenol | 133 | 115 |
| 0.005% | 137 | 137 |
| 0.01% | 135 | 126 |
| 0.03% | 127 | 130 |
| 0.05% | 133 | 137 |
| 0.1% | 133 | 132 |
| 0.3% | 124 | 123 |
| 0.5% | 120 | 117 |
| 1.0% | 120 | 97 |
| 2.0% | 61 | 60 |
| 0.001% 4-bromophenol | 140 | 138 |
| 0.005% | 133 | 140 |
| 0.01% | 139 | 140 |
| 0.03% | 137 | 135 |
| 0.05% | 145 | 143 |
| 0.1% | 158 | 160 |
| 0.3% | 185 | 177 |
| 0.5% | 172 | 138 |
| 0.5%: buffer solution saturated with 4 bromophenol | | |
| 0.001% 2,4-dichlorophenol | 130 | 129 |
| 0.005% | 140 | 146 |
| 0.01% | 137 | 137 |
| 0.03% | 130 | 133 |
| 0.05% | 143 | 145 |
| 0.05%: buffer solution saturated with 2,4-dichlorophenol | | |

What is claimed is:

1. A process for stabilizing the activity of peroxidase enzyme in solution by the addition of a specific activity stabilizer comprising adding to the enzyme in solid or dissolved form, as the activity stabilizer, phenol which is unsubstituted or is substituted with one or more substituents selected from the group consisting of $C_1$-$C_3$ lower alkyl, chlorine and bromine, in an amount of form 0.0005 to 2% by weight, referred to the solution and wherein the peroxidase is used as a conjugate with an immunologically active substance.

2. The process of claim 1, wherein 0.01 to 0.05% by weight of phenol are added.

3. The process of claim 1 further comprising, after the phenol is added, lyophilizing the solution.

4. The process of claim 1, wherein the enzyme is in the form of a lyophilizate which has been reconstituted in aqueous solvent and the phenol is added to the reconstituted lyophilisate.

5. The process of claim 1 wherein the peroxidase is conjugated with an immunologically-active substance.

6. The process of claim 5, wherein the immunologically-active substance is an antibody or a fragment thereof, an antigen or a hapten.

7. The process of claim 6, wherein the immunologically-active substance is digoxin, digoxigenin, triiodothyronine or thyroxin or an antibody against TSH, ferritin or AFP.

8. A stabilized peroxidase enzyme preparation comprising peroxidase and 0.0005 to 2% by weight of phenol or phenol substituted with one or more substituents selected from the group consisting of $C_1$-$C_3$ lower alkyl, chlorine and bromine, wherein the peroxidase is conjugated with an immunologically active substance.

9. The stabilized peroxidase enzyme preparation of claim 8 wherein the immunologically active substance is an antibody or fragment thereof, an antigen or a hapten.

10. The stabilized peroxidase enzyme preparation of claim 8 wherein the immunologically active substance is digoxin, digoxigenin, triiodothyronine, thyroxin or an antibody against TSH, ferritin or AFP.

11. The stabilized peroxidase enzyme preparation of claim 8 wherein phenol is used.

12. The stabilized peroxidase enzyme preparation of claim 8 wherein phenol substituted one or two times is used.

13. The stabilized peroxidase enzyme preparation of claim 12 wherein bromophenol, chlorophenol, dichlorophenol, dibromophenol or cresol is used.

* * * * *